United States Patent
Herrig

(10) Patent No.: US 9,278,172 B2
(45) Date of Patent: Mar. 8, 2016

(54) VASCULAR ACCESS SYSTEM WITH CONNECTOR

(75) Inventor: Judson A. Herrig, Elko, MN (US)

(73) Assignee: CRYOLIFE, INC., Kennesaw, GA (US)

( * ) Notice: Subject to any disclaimer, the term of this patent is extended or adjusted under 35 U.S.C. 154(b) by 612 days.

(21) Appl. No.: 13/605,678

(22) Filed: Sep. 6, 2012

(65) Prior Publication Data

US 2013/0060268 A1    Mar. 7, 2013

Related U.S. Application Data

(60) Provisional application No. 61/531,303, filed on Sep. 6, 2011, provisional application No. 61/636,851, filed on Apr. 23, 2012.

(51) Int. Cl.
| | |
|---|---|
| *A61B 17/08* | (2006.01) |
| *A61M 1/36* | (2006.01) |
| *A61M 39/12* | (2006.01) |
| *A61M 1/10* | (2006.01) |
| *A61B 17/11* | (2006.01) |
| *A61M 39/10* | (2006.01) |

(52) U.S. Cl.
CPC ............ *A61M 1/3655* (2013.01); *A61M 1/1008* (2014.02); *A61M 39/12* (2013.01); *A61B 17/11* (2013.01); *A61B 2017/1132* (2013.01); *A61M 39/10* (2013.01)

(58) Field of Classification Search
CPC .......... A61B 17/11; A61B 2017/1132; A61M 1/1008
See application file for complete search history.

(56) References Cited

U.S. PATENT DOCUMENTS

| | | | |
|---|---|---|---|
| 3,363,926 A | | 1/1968 | Wilson |
| 3,435,823 A | * | 4/1969 | Edwards .................... 606/153 |
| 3,490,438 A | | 1/1970 | Lavender et al. |
| 3,814,137 A | | 6/1974 | Martinez |
| 3,818,511 A | | 6/1974 | Goldberg |
| 3,826,257 A | | 7/1974 | Buselmeier |
| 3,882,862 A | | 5/1975 | Berend |

(Continued)

FOREIGN PATENT DOCUMENTS

| | | |
|---|---|---|
| DE | 4418910 A1 | 12/1995 |
| DE | 29515546 U1 | 1/1997 |

(Continued)

OTHER PUBLICATIONS

International Search Report and Written Opinion for International Application No. PCT/US2012/053967 mailed May 3, 2013.

(Continued)

*Primary Examiner* — Robert Lynch
(74) *Attorney, Agent, or Firm* — Sutherland Asbill & Brennan LLP

(57) ABSTRACT

A connector for fluidly coupling proximal and distal tubular segments of a fluid conduit is provided. In one embodiment, the connector can include a connector body having an outer surface defining a first outer perimeter and an inner surface defining a lumen. The connector can also include a connecting device having an open configuration and a plurality of closed configurations. The connecting device can include first and second members configured to engage each other to secure the fluid conduit to the connector. The connecting device can also include a plurality of closed configurations for securing fluid conduits of different sizes.

25 Claims, 9 Drawing Sheets

(56) References Cited

U.S. PATENT DOCUMENTS

| | | | |
|---|---|---|---|
| 3,998,222 A | 12/1976 | Shihata |
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmerman |
| 4,427,219 A | 1/1984 | Madej |
| 4,441,215 A | 4/1984 | Kaster |
| 4,447,237 A | 5/1984 | Frisch et al. |
| 4,496,349 A | 1/1985 | Costentino |
| 4,496,350 A | 1/1985 | Costentino |
| 4,503,568 A | 3/1985 | Madras |
| 4,550,447 A | 11/1985 | Seiler et al. |
| 4,619,641 A | 10/1986 | Schanzer |
| 4,655,771 A | 4/1987 | Wallsten |
| 4,734,094 A | 3/1988 | Jacob et al. |
| 4,753,236 A | 6/1988 | Healey |
| 4,771,777 A | 9/1988 | Horzewski et al. |
| 4,772,268 A | 9/1988 | Bates |
| 4,786,345 A | 11/1988 | Wood |
| 4,790,826 A | 12/1988 | Elftman |
| 4,822,341 A | 4/1989 | Colone |
| 4,848,343 A | 7/1989 | Wallersten et al. |
| 4,850,999 A | 7/1989 | Planck |
| 4,856,938 A | 8/1989 | Kuehn |
| 4,877,661 A | 10/1989 | House et al. |
| 4,898,669 A | 2/1990 | Tesio |
| 4,917,067 A | 4/1990 | Yoshida |
| 4,917,087 A | 4/1990 | Walsh et al. |
| 4,919,127 A | 4/1990 | Pell |
| 4,929,236 A | 5/1990 | Sampson |
| 4,955,899 A | 9/1990 | Della et al. |
| 5,026,513 A | 6/1991 | House et al. |
| 5,041,098 A | 8/1991 | Loiterman et al. |
| 5,053,023 A | 10/1991 | Martin |
| 5,061,275 A | 10/1991 | Wallersten et al. |
| 5,061,276 A | 10/1991 | Tu et al. |
| 5,064,435 A | 11/1991 | Porter |
| 5,104,402 A | 4/1992 | Melbin |
| 5,171,227 A | 12/1992 | Twardowski et al. |
| 5,171,305 A | 12/1992 | Schickling et al. |
| 5,192,289 A | 3/1993 | Jessen |
| 5,192,310 A | 3/1993 | Herweck et al. |
| 5,197,976 A | 3/1993 | Herweck et al. |
| 5,330,500 A | 7/1994 | Song |
| 5,361,748 A | 11/1994 | Matteucci |
| 5,399,168 A | 3/1995 | Wadsworth et al. |
| 5,405,320 A | 4/1995 | Twardowski et al. |
| 5,405,339 A | 4/1995 | Kohnen et al. |
| 5,454,790 A | 10/1995 | Dubrul |
| 5,474,268 A * | 12/1995 | Yu ................................... 248/61 |
| 5,476,451 A | 12/1995 | Ensminger et al. |
| 5,496,294 A | 3/1996 | Hergenrother et al. |
| 5,509,897 A | 4/1996 | Twardowski et al. |
| 5,558,641 A | 9/1996 | Glantz et al. |
| 5,562,617 A | 10/1996 | Finch et al. |
| 5,562,618 A | 10/1996 | Cai et al. |
| 5,591,226 A | 1/1997 | Trerotola et al. |
| 5,607,463 A | 3/1997 | Schwartz et al. |
| 5,624,413 A | 4/1997 | Markel et al. |
| 5,631,748 A | 5/1997 | Harrington |
| 5,637,088 A | 6/1997 | Wenner |
| 5,637,102 A | 6/1997 | Tolkoff et al. |
| 5,645,532 A | 7/1997 | Horgan |
| 5,647,855 A | 7/1997 | Trooskin |
| 5,669,637 A | 9/1997 | Chitty et al. |
| 5,669,881 A | 9/1997 | Dunshee |
| 5,674,272 A | 10/1997 | Bush et al. |
| 5,676,346 A | 10/1997 | Leinsing |
| 5,743,894 A | 4/1998 | Swisher |
| 5,755,773 A | 5/1998 | Evans et al. |
| 5,755,775 A | 5/1998 | Trerotola et al. |
| 5,792,104 A | 8/1998 | Speckman et al. |
| 5,797,879 A | 8/1998 | DeCampli |
| 5,800,512 A | 9/1998 | Lentz et al. |
| 5,800,514 A | 9/1998 | Nunez et al. |
| 5,800,522 A | 9/1998 | Campbell et al. |
| 5,810,870 A | 9/1998 | Myers et al. |
| 5,829,487 A | 11/1998 | Thomas et al. |
| 5,830,224 A | 11/1998 | Cohn et al. |
| 5,840,240 A | 11/1998 | Stenoien et al. |
| 5,866,217 A | 2/1999 | Stenoien et al. |
| 5,904,967 A | 5/1999 | Ezaki et al. |
| 5,931,829 A | 8/1999 | Burbank et al. |
| 5,931,865 A | 8/1999 | Silverman et al. |
| 5,957,974 A | 9/1999 | Thompson et al. |
| 5,997,562 A | 12/1999 | Zadno-Azizi et al. |
| 6,001,125 A | 12/1999 | Golds et al. |
| 6,019,788 A | 2/2000 | Butters et al. |
| 6,036,724 A | 3/2000 | Lentz et al. |
| 6,102,884 A | 8/2000 | Squitieri |
| 6,156,016 A | 12/2000 | Maginot |
| 6,167,765 B1 | 1/2001 | Weitzel |
| 6,171,295 B1 | 1/2001 | Garabedian |
| 6,231,085 B1 | 5/2001 | Olson |
| 6,245,098 B1 | 6/2001 | Feeser |
| 6,255,396 B1 | 7/2001 | Ding et al. |
| 6,261,255 B1 | 7/2001 | Mullis et al. |
| 6,261,257 B1 | 7/2001 | Uflacker et al. |
| 6,319,279 B1 | 11/2001 | Shannon et al. |
| 6,338,724 B1 | 1/2002 | Dossa |
| 6,398,764 B1 | 6/2002 | Finch et al. |
| 6,402,767 B1 | 6/2002 | Nash et al. |
| 6,428,571 B1 | 8/2002 | Lentz et al. |
| 6,436,132 B1 | 8/2002 | Patel et al. |
| 6,536,135 B2 | 3/2003 | Lipkin |
| 6,582,409 B1 | 6/2003 | Squitieri |
| 6,585,762 B1 | 7/2003 | Stanish |
| 6,610,004 B2 | 8/2003 | Viole et al. |
| 6,689,096 B1 | 2/2004 | Loubens et al. |
| 6,689,157 B2 | 2/2004 | Madrid et al. |
| 6,692,461 B2 | 2/2004 | Wantink |
| 6,699,233 B2 | 3/2004 | Slanda |
| 6,702,748 B1 | 3/2004 | Nita et al. |
| 6,702,781 B1 | 3/2004 | Reifart et al. |
| 6,706,025 B2 | 3/2004 | Engelson et al. |
| 6,719,781 B1 | 4/2004 | Kim |
| 6,719,783 B2 | 4/2004 | Lentz et al. |
| 6,730,096 B2 | 5/2004 | Basta et al. |
| 6,733,459 B1 | 5/2004 | Atsumi |
| 6,740,273 B2 | 5/2004 | Lee |
| 6,749,574 B2 | 6/2004 | O'Keefe |
| 6,752,826 B2 | 6/2004 | Holloway |
| 6,758,836 B2 | 7/2004 | Zawacki |
| 6,858,019 B2 | 2/2005 | McGuckin |
| 6,926,735 B2 | 8/2005 | Henderson |
| 6,976,952 B1 | 12/2005 | Maini |
| 7,011,645 B2 | 3/2006 | McGuckin |
| 7,025,741 B2 | 4/2006 | Cull |
| 7,036,599 B2 | 5/2006 | Matteucci |
| 7,101,356 B2 | 9/2006 | Miller |
| 7,131,959 B2 | 11/2006 | Blatter |
| 7,211,074 B2 | 5/2007 | Sansoucy |
| 7,244,271 B2 | 7/2007 | Lentz et al. |
| 7,244,272 B2 | 7/2007 | Dubson et al. |
| 7,252,649 B2 | 8/2007 | Sherry |
| 7,297,158 B2 | 11/2007 | Jensen |
| 7,399,296 B2 | 7/2008 | Poole et al. |
| 7,438,699 B2 | 10/2008 | Pecor et al. |
| 7,452,374 B2 | 11/2008 | Hian et al. |
| 7,507,229 B2 | 3/2009 | Hewitt et al. |
| 7,588,551 B2 | 9/2009 | Gertner |
| 7,708,722 B2 | 5/2010 | Glenn |
| 7,722,665 B2 | 5/2010 | Anwar et al. |
| RE41,448 E | 7/2010 | Squitieri |
| 7,762,977 B2 | 7/2010 | Porter et al. |
| 7,789,908 B2 | 9/2010 | Sowinski et al. |
| 7,828,833 B2 | 11/2010 | Haverkost et al. |
| 7,833,214 B2 | 11/2010 | Wilson et al. |
| 7,846,139 B2 | 12/2010 | Zinn et al. |
| 7,850,675 B2 | 12/2010 | Bell et al. |
| 7,850,705 B2 | 12/2010 | Bachinski et al. |
| 7,922,757 B2 | 4/2011 | McGuckin |
| 7,972,314 B2 | 7/2011 | Bizup et al. |

(56) References Cited

U.S. PATENT DOCUMENTS

| | | |
|---|---|---|
| 8,079,973 B2 | 12/2011 | Herrig et al. |
| 8,092,435 B2 | 1/2012 | Beling et al. |
| 8,097,311 B2 | 1/2012 | Wang et al. |
| 8,313,524 B2 | 11/2012 | Edwin et al. |
| 2002/0049403 A1 | 4/2002 | Alanis |
| 2003/0100859 A1 | 5/2003 | Henderson et al. |
| 2003/0212385 A1 | 11/2003 | Brenner et al. |
| 2004/0073282 A1 | 4/2004 | Stanish |
| 2005/0137614 A1 | 6/2005 | Porter et al. |
| 2005/0192559 A1 | 9/2005 | Michels et al. |
| 2005/0203457 A1 | 9/2005 | Smego |
| 2005/0215938 A1 | 9/2005 | Khan et al. |
| 2006/0058867 A1 | 3/2006 | Thistle et al. |
| 2006/0064159 A1 | 3/2006 | Porter et al. |
| 2006/0081260 A1 | 4/2006 | Eells et al. |
| 2006/0118236 A1 | 6/2006 | House |
| 2007/0078412 A1 | 4/2007 | McGuckin et al. |
| 2007/0078416 A1 | 4/2007 | Eliasen |
| 2007/0078438 A1 | 4/2007 | Okada |
| 2007/0088336 A1 | 4/2007 | Dalton |
| 2007/0123811 A1 | 5/2007 | Squitieri |
| 2007/0135775 A1 | 6/2007 | Edoga et al. |
| 2007/0167901 A1 | 7/2007 | Herrig et al. |
| 2007/0191779 A1 | 8/2007 | Shubayev et al. |
| 2007/0197856 A1 | 8/2007 | Gellman et al. |
| 2007/0213838 A1 | 9/2007 | Hengelmolen |
| 2007/0249986 A1 | 10/2007 | Smego |
| 2007/0265584 A1 | 11/2007 | Hickman et al. |
| 2007/0293829 A1 | 12/2007 | Conlon et al. |
| 2008/0167595 A1 | 7/2008 | Porter et al. |
| 2008/0221469 A1* | 9/2008 | Shevchuk .................... 600/532 |
| 2008/0306580 A1 | 12/2008 | Jenson |
| 2009/0076587 A1 | 3/2009 | Cully et al. |
| 2009/0137944 A1 | 5/2009 | Haarala et al. |
| 2009/0318895 A1 | 12/2009 | Lachner |
| 2010/0268196 A1 | 10/2010 | Hastings et al. |
| 2011/0054312 A1 | 3/2011 | Bell et al. |
| 2011/0208218 A1 | 8/2011 | Ball |
| 2011/0257609 A1 | 10/2011 | Bizup et al. |
| 2011/0264080 A1 | 10/2011 | Lim et al. |
| 2012/0078202 A1 | 3/2012 | Beling et al. |

FOREIGN PATENT DOCUMENTS

| | | |
|---|---|---|
| JP | 57-14358 | 1/1982 |
| JP | 62-112567 | 5/1987 |
| JP | 06-105798 | 4/1994 |
| JP | 0984871 | 3/1997 |
| WO | 8403036 A1 | 8/1984 |
| WO | 9519200 A1 | 7/1995 |
| WO | 9624399 A1 | 8/1996 |
| WO | WO9834676 | 8/1998 |
| WO | 00/27299 A1 | 5/2000 |
| WO | 0076577 A1 | 12/2000 |
| WO | 0105463 A1 | 1/2001 |
| WO | WO0128456 | 4/2001 |
| WO | 2004/032991 A2 | 4/2004 |
| WO | 2004112880 A1 | 12/2004 |
| WO | 2011/060386 A2 | 5/2011 |

OTHER PUBLICATIONS

PCT International Preliminary Report on Patentability issued Mar. 12, 2014 for International Application No. PCT/US2012/053967.

European Search Report dated Dec. 3, 2013.

* cited by examiner

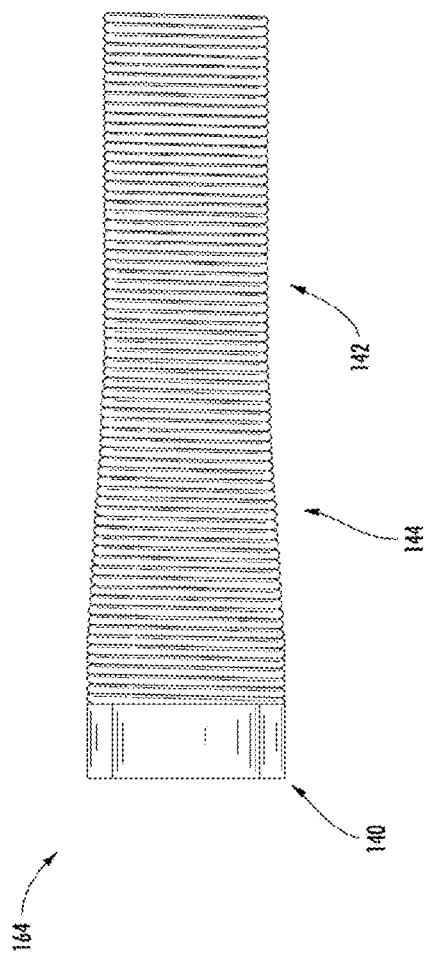
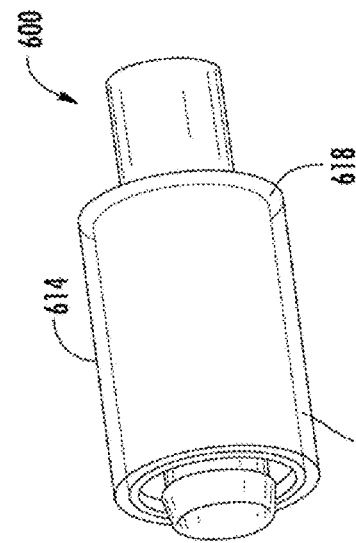
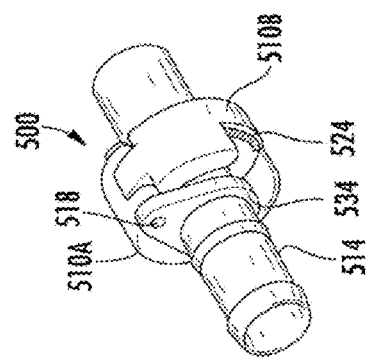
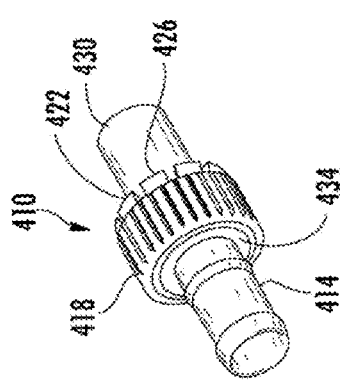

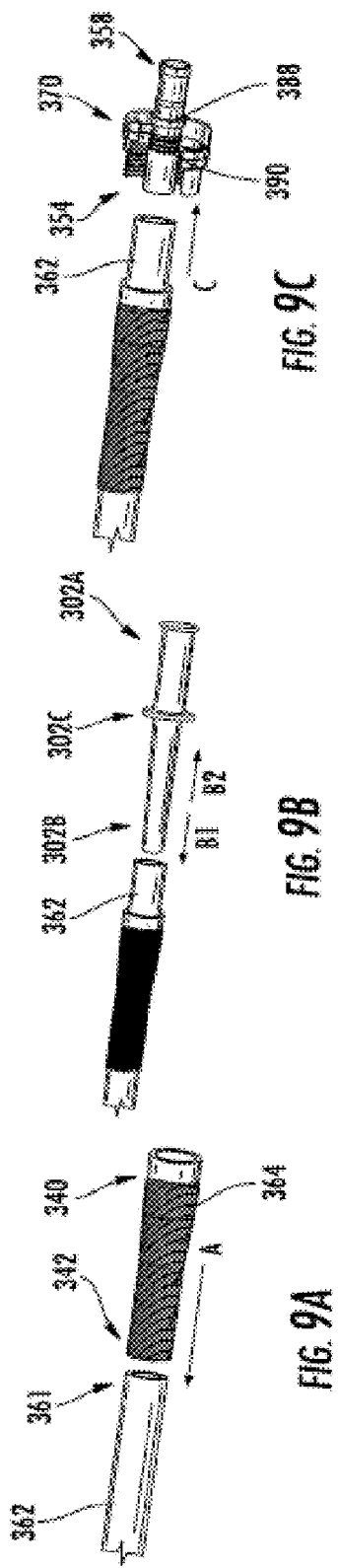

VASCULAR ACCESS SYSTEM WITH CONNECTOR

CROSS-REFERENCE TO RELATED APPLICATIONS

This application claims the benefit of and is a non-provisional of U.S. Provisional Patent Application No. 61/531,303, filed Sep. 6, 2011, and U.S. Provisional Patent Application No. 61/636,851, filed Apr. 23, 2012, which are both hereby incorporated by reference.

BACKGROUND

This application relates to a connector which can be included in a system for connecting multiple portions of a fluid carrying conduit.

In the United States, approximately 400,000 people have end-stage renal disease requiring chronic hemodialysis. Permanent vascular access sites for performing hemodialysis may be formed by creating an arteriovenous (AV) anastomosis whereby a vein is attached to an artery to form a high-flow shunt or fistula. A vein may be directly attached to an artery, but it may take 6 to 8 weeks before the venous section of the fistula has sufficiently matured to provide adequate blood flow for use with hemodialysis. Moreover, a direct anastomosis may not be feasible in all patients due to anatomical considerations.

Other patients may require the use of artificial graft material to provide an access site between the arterial and venous vascular systems. Patency rates of grafts are still not satisfactory, as the overall graft failure rate remains high. Temporary catheter access is also an option. However, the use of temporary catheter access exposes the patient to additional risk of bleeding and infection, as well as discomfort.

SUMMARY

Some or all of the above needs and/or problems may be addressed by certain embodiments disclosed herein. For example, in one embodiment, a system is provided for providing continuous flow of blood between two locations in a patient's cardiovascular system. A blood conduit is provided that has a distal portion and a proximal portion. The distal portion is adapted to be inserted into a blood vessel at an insertion site and to be advanced therethrough to a location spaced apart from the insertion site. The system is provided with a connector that has a distal portion adapted to be engaged with the proximal portion of the blood conduit and a tubular body extending proximally of the distal portion. The tubular body is adapted to be inserted into an end of a vascular graft. The connector is provided with a connecting device having an open configuration. The connecting device also has a first closed configuration providing a first gap between an inner surface of the connecting device and the tubular body and a second closed configuration providing a second gap between the inner surface of the connecting device and the tubular body. The first gap accommodates a graft having an inner perimeter matching the outer perimeter of the tubular body and a first wall thickness. The second gap accommodates a graft having an inner perimeter matching the outer perimeter of the tubular body and a second wall thickness different than the first wall thickness. Continuous flow can be provided from grafts of different wall thicknesses through the connector and into the blood conduit.

Other embodiments, aspects, and features of the disclosure will become apparent to those skilled in the art from the following detailed description, the accompanying drawings, and the appended claims.

BRIEF DESCRIPTION OF THE DRAWINGS

The structure and method of using the invention will be better understood with the following detailed description of embodiments of the invention, along with the accompanying illustrations, which are not necessarily drawn to scale.

FIG. 7 is a plan view of an embodiment of a strain relief structure.

FIG. 8A is a perspective view of a connector device utilizing a proximal longitudinal motion of an outer ring to secure any of a range of blood conduit components.

FIG. 8B is a perspective view of a connector comprising a clamshell construction that can be used to secure any of a range of blood conduit components.

FIG. 8C is a perspective view of a connector having a sprung member to secure any of a range of blood conduit components.

FIGS. 9A-9F illustrate example systems and method for facilitating a connection.

DETAILED DESCRIPTION

Improved hemodialysis and vascular access systems and methods have been developed. In one broad sense, certain embodiments include a blood flow component that can be used for outflow of blood from the system and a coupling or connecting device that can be used to secure an inflow conduit of the system relative to the outflow conduit. Secure connection of the inflow and outflow components enable a continuous flow through the system, where the inflow and outflow components are in secure fluid communication with each other. Techniques for connecting the outflow component with the connecting device are also provided. In various embodiments, the connective device and assembly methods improve over, and/or build upon, the connecting means described in U.S. Pat. No. 8,079,973, which is hereby incorporated by reference.

A proximal portion of the connecting device is provided in various embodiments to enable fluid connection of the outflow component with any of a variety of inflow components. The inflow components can be any of a variety of blood conduits that are able to be connected to the vascular system to receive blood into the vascular access system. Such blood conduits can have a construction similar to a vascular graft made of ePTFE, Dacron, or other suitable materials. Other suitable materials can include a material that is biocompatible with an artery and has a non- or minimally thrombogenic characteristic. The inflow component preferably is adapted for long term attachment to an artery. The inflow component preferably comprises a region suitable for repeated needle access. For example, a length of the inflow component can be configured to be pierced by a needle to enable blood to be withdrawn from and returned to the system. While packaging an outflow component with a connector is convenient to the manufacturer, different end users may have different preferences regarding which inflow component to use. For example, some end users may prefer one material or manufacturer over others for any of a variety of reasons.

Accordingly, to enable the outflow component to be used with a wide variety of grafts and other inflow components, connecting devices have been developed and are provided herein that are connectable to a variety of grafts and other inflow components.

Figure 1:
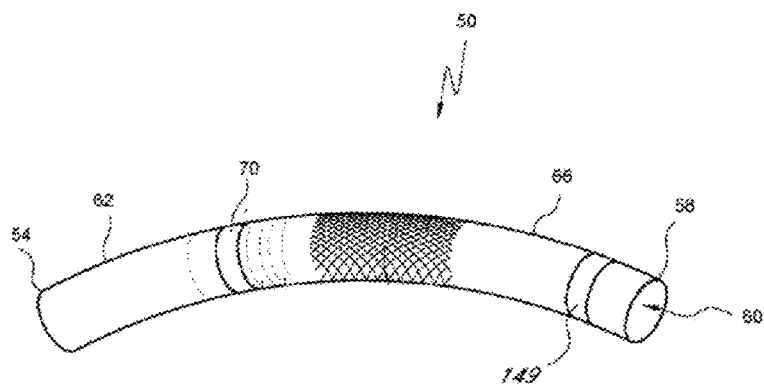
FIG. 1 is a perspective view of an embodiment of a vascular access system.

FIG. 1 illustrates one embodiment of a vascular access system 50 having a plurality of components that can be assembled together to form a lumen 60. The lumen 60 provides a blood conduit or pathway configured to shunt blood from a first vascular segment to a second vascular segment. The vascular access system 50 has a proximal end 54 and a distal end 58 and a lumen 60 that extends between the proximal and distal ends 54, 58. In some embodiments, the proximal end 54 can be adapted to couple with, e.g., attached to, a first vascular segment and the distal end 58 can be adapted to be coupled with, e.g., inserted into a second vascular segment. The lumen 60 preferably extends between the proximal and distal ends 54, 58. The lumen 60 can also be accessed from outside the patient to facilitate dialysis or other treatment.

In one embodiment, as illustrated in FIG. 1, the vascular access system includes a connector 70 adapted to fluidly connect a first conduit 62, such as an inflow component or graft, and a second conduit 66, such as an outflow component or catheter, to form the lumen 60. In certain embodiments, the first conduit 62 extends from the proximal end 54 toward the distal end 58, and the second conduit extends from the distal end 58 toward the proximal end 54. The connector 70 can be positioned between the first and second conduits 62, 66 such that a distal portion of the first conduit 62 is configured to be connected to a proximal portion of connector 70 and a proximal portion of the second conduit 66 is configured to be connected to a distal portion of connector 70. The connector 70 and/or conduits 62, 66 can be provided and/or integrated with one or more connecting devices to connect or enhance the security of connection between the first and second conduits 62, 66.

Figure 2:
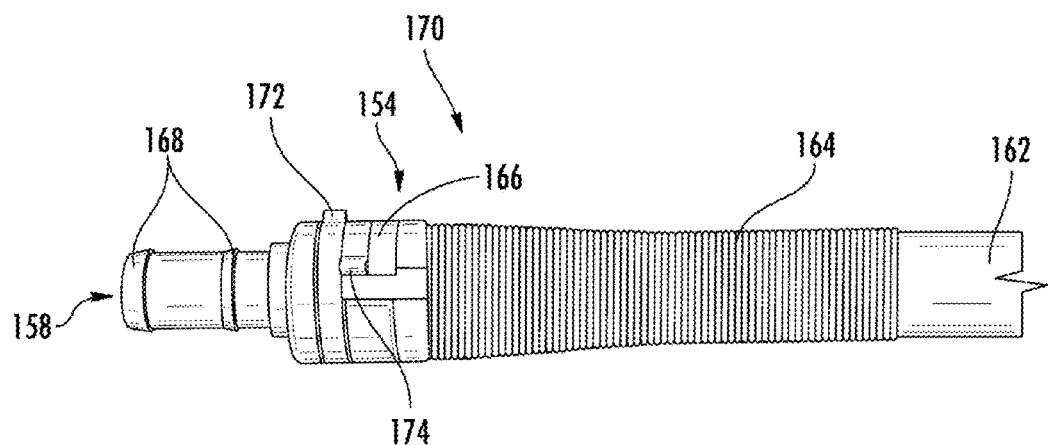
FIG. 2 is a plan view of an embodiment of a vascular access system assembly including a connector, a strain relief structure, and a vascular graft.

FIG. 2 illustrates a sub-assembly of one embodiment of a vascular access system assembly similar to that of FIG. 1. FIG. 2 shows a system including a connector 170 and an inflow component 162. The inflow component 162 can take a variety of configurations, for example, having wall thickness in a relatively wide range, but otherwise similar to a vascular graft. The inflow component 162 is connected to and in fluid communication with a portion of a first end 154 of the connector 170 via a connecting device 166. A portion of a second end 158 of the connector 170 can be connected to an outflow component, such as a blood conduit or catheter. The outflow component can be similar to the outflow component 66, described in more detail in U.S. Pat. No. 8,079,973, which is hereby incorporated by reference. As illustrated in FIG. 2, in some embodiments, the second end 158 of the connector 170 can have a tubular structure with one or more engagement features 168 to enhance the security of connection or provide mechanical engagement between the connector 170 and the outflow component. The engagement features 168 can have enlarged outer diameters or perimeters greater than the diameter of the tubular structure of the second end 158 of the connector 170. In some embodiments, the engagement features 168 can comprise one or more barbs. As illustrated, in some embodiments, the engagement features 168 can have conical shapes with the outer perimeter or diameter increasing from a first end to a second end of an engagement feature 168. In some embodiments, the connecting device 166 can have a clamshell structure. The term clamshell structure is a broad term intended to cover a combination of a plurality of members, at least one of which can pivot away from and toward the other, wherein when pivoted together a closed configuration is formed, and is not limited to structures with clamshell type shapes or edge-to-edge contact around a perimeter. For example, in some embodiments, the hinge-type mechanism can have arcuate finger-shaped members or have members with outer diameters or surfaces that are more angular or square in shape and inner diameters or surfaces more tubular or cylindrical in shape. In this manner, the connecting device 166 may be any configuration that performs its intended function.

Figure 11:
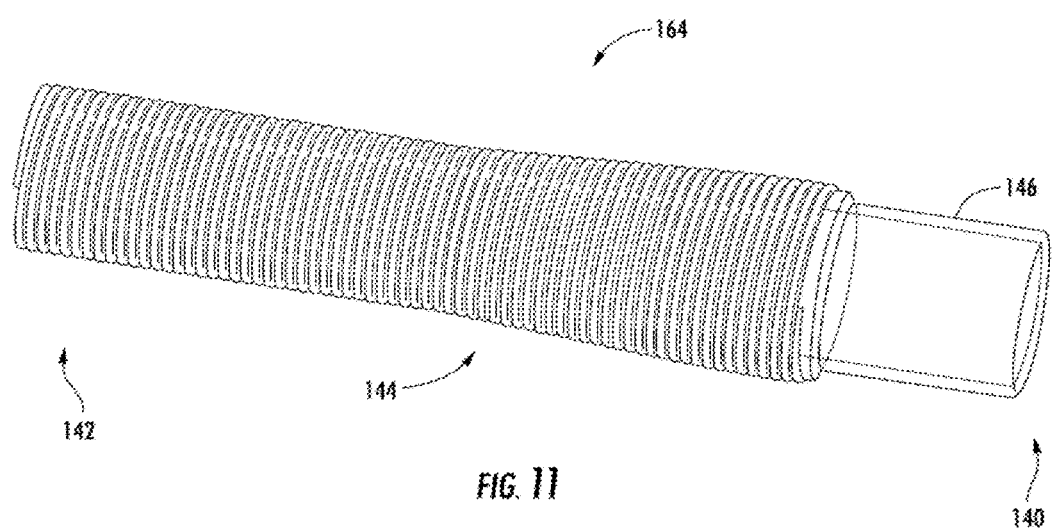
FIG. 11 is a perspective view of an embodiment of a strain relief structure.

In some embodiments, as illustrated in FIGS. 2, 7, and 11 the system or assembly can be provided with one or more strain relief structures 164 surrounding the inflow component 162 and/or an outflow component. In some embodiments, the strain relief structure 164 comprises an elastomeric sleeve that can be slid over a portion of the first end of the connector and a coil that surrounds the inflow component. The sleeve enables the strain relief structure 164, which can be a coil or other structure reducing or minimizing strain on the inflow component by the connector. The elastomeric properties allow the sleeve to couple with the connector when it exhibits a range of outer diameters, depending on wall thickness of attached inflow component, as discussed in more detail below. In other embodiments, the strain relief structure 164 can be configured to have a mechanically varying inner profile that does not rely on elastomeric properties to accept larger and smaller structures due to the varying of the wall thickness or other transverse dimension of the inflow component or connector. However, the elastomeric sleeve is a simple structure that requires few parts and thus is an elegant solution to the problem of coupling a strain relief structure to the connector, which can have different outer perimeters and configurations in use.

The strain relief structure 164 reduces or minimizes kinking or pinching of the inflow component 162. In some embodiments, the strain relief structure 164 can include both a resilient characteristic and a soft inner surface. For example, a springy material or configuration, such as a nitinol coil can be provided to resist unwanted, unpredictable deformation in the zone of the strain relief structure 164. Also, a soft material or construction, such as a silicone sleeve can be provided to isolate the inflow component 162 from pinching due to kinking. In some instances, the sleeve can be slid over an end of the connecting device 166 forming a friction fit with the connecting device 166 and a slip fit with the inflow component 162. In other instances, the sleeve can be clamped within the connecting device 166 to form a mechanical connection between the sleeve and the connecting device 166. As discussed above, in some embodiments, this can help prevent kinking or closing of the inflow component 162 as it extends out from the connecting device 166.

Figure 3:
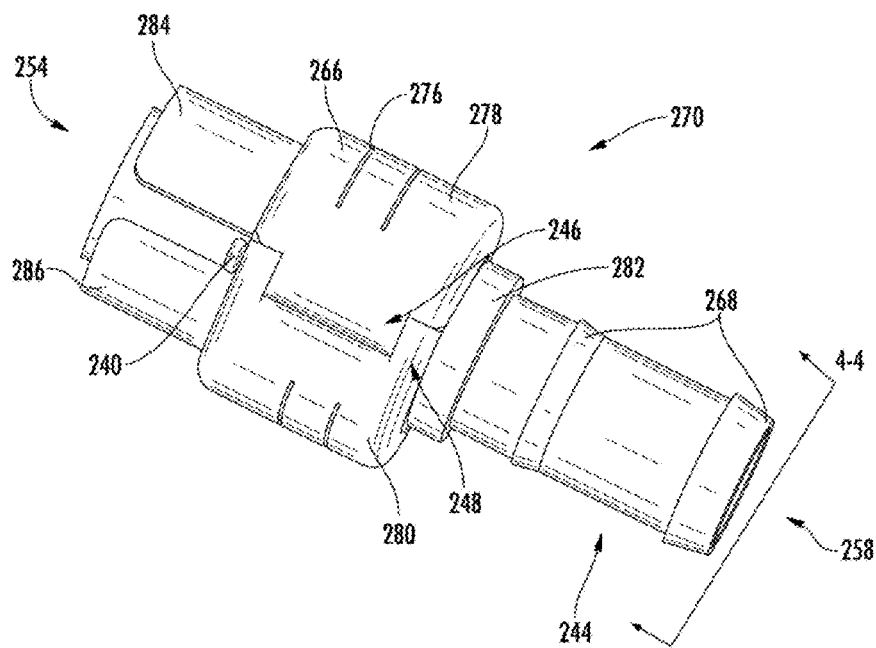
FIG. 3 is a perspective view of an embodiment of a connector in a closed configuration.

FIG. 3 illustrates one embodiment of a connector 270. As illustrated, the connector 270 is in a closed configuration. In some embodiments, a connecting device 266 can be integrated with the connector 270. In other embodiments, the connecting device 266 can be a separate component from the connector 270. The connector 270 can be configured with a flange 282 or protrusion to which a hinge structure 240, such as a pin can be mounted. The flange 282 can be configured as a radially projected member of the connector 270, in some embodiments forming a widest profile of the connector 270.

The connecting device 266 can be provided with first and second members 278, 280 that have first and second ends 246, 248 and 250, 252 respectively. The first ends 246, 248 of the first and second members 278, 280 of the connecting device 266 can be pivotably coupled with the hinge structure at the flange 282 of the connector 270. The second ends 250, 252 (see FIG. 4) can be positioned or disposed away from the first ends 246, 248. The first and second members 278, 280 have a combination of rigidity and flexibility to permit relatively easy coupling and very secure connection therebetween.

Some flexibility in a direction parallel to the longitudinal axis of the lumen defined within the connector 270 can be provided by slots 276 disposed adjacent to the second ends 250, 252 of each of the members 278, 280. The slots 276 can start at the second ends 250, 252 and extend toward the first ends 246, 248. As discussed further below, the slots 276 enable teeth disposed on the second ends 250, 252 of the first and second members 278, 280 to be deflected axially by an amount sufficient to permit the teeth to move circumferentially past each other. The slots are one example of an axial displacement feature, which can take other forms, such as including channels or recesses positioned on at least a portion of a surface of the first and second members 278, 280. In various embodiments, the axial displacement feature can extend at least a portion of the distance between the second and first ends 250, 252 and 246, 248 of at least one of the first and second members 278, 280. For example, in one embodiment, the axial displacement feature can be configured to extend at least about 25% of the distance between the second and first ends 250, 252 and 246, 248 of at least one of the first and second members 278, 280. More generally, these structures are configured to enable some degree of flex in the first and second members 278, 280 while generally minimizing yield of these members so that the force applied therebetween is known or within an acceptable range.

The connecting device 266 can have proximally extending shrouds 284, 286 that extend out from a side of the first and second members 278, 280 towards a first end 254 of the connector 270. The shrouds 284, 286 are discussed in more detail in connection with FIG. 4 below. In some embodiments, the shrouds 284, 286 can be omitted, or otherwise substantially reduced, as discussed in more detail in connection with FIG. 10 below.

As discussed above, the connector 270 can have a tubular structure 244 extend out towards a second end 258. The tubular structure 244 can be adapted to be connected with an outflow component, illustrated in FIG. 1. The tubular structure 244 can be provided with engagement features 268 for secure attachment with the outflow component as discussed in greater detail in U.S. Pat. No. 8,079,973, previously incorporated by reference herein.

Figure 4:
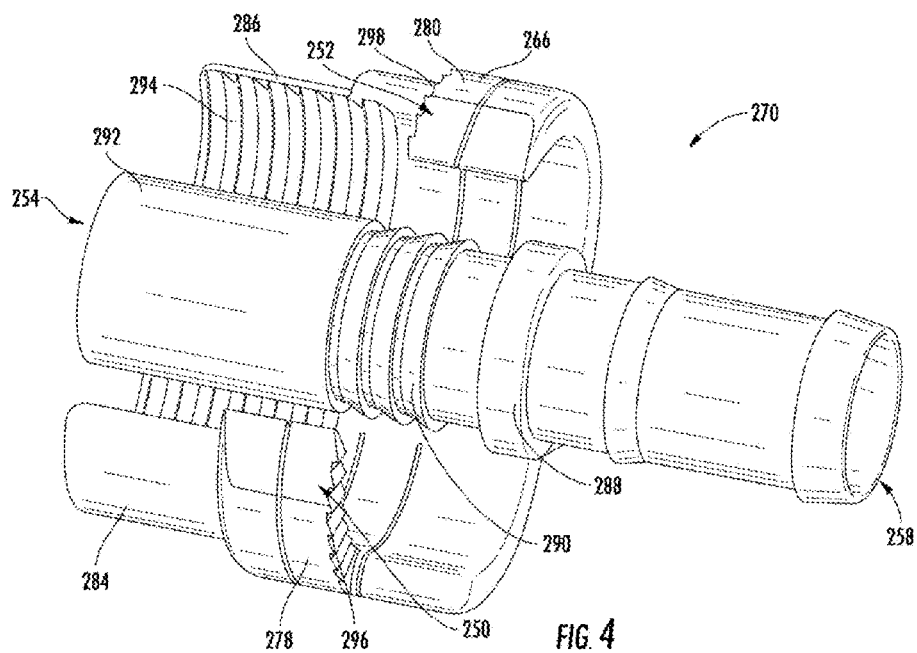
FIG. 4 is a perspective view of an embodiment of a connector in an open configuration.

FIG. 4 illustrates one embodiment of the connector 270 in an open configuration. The first and second members 278, 280 of the connecting device 266 are configured to engage portions of an outer surface of an inflow component or graft (not shown) to secure it to the connector 270. A range of positions or closed configurations for the first and second members 278, 280 are provided such that a range of thicknesses of grafts can be secured to the connector 270. The ability to accept ranges of thicknesses enables the connector 270 to work with different distributions of products, e.g., having average wall thicknesses at least at their distal ends that are significantly different. As discussed elsewhere herein, this feature advantageously enables a system including the connector 270 to be used in more settings and with various different products in a product line. In some embodiments, the second ends 250, 252 of the first and/or second members 278, 280 of the connecting device 266 can be provided with protrusions, gripping structures or teeth 296, 298 on mating surfaces that maintain compressive force on the graft and connector in the closed configurations. The teeth 296, 298 can be formed along an arcuate body on the first and second members 278, 280, allowing a secured or locked engagement at any position over an arcuate path of movement of the first and second members 278, 280. As discussed above, first ends 246, 248 of the first and second members 278, 280 can be pivotably connected at one axis of rotation, such as by a pin 240.

In some embodiments, to facilitate engagement of the teeth 296, 298 some axial displacement of at least a portion of at least one of the first and second members 278, 280 can be provided. For example, the slot 276 can enable the second ends 250, 252 of the first and second members 278, 280 to deflect away from each other by an amount sufficient to enable the teeth to slide past each other when so deflected. In one example, the slots 276 can enable the second ends 250, 252 of each of the first and second members 278, 280 to deflect at least about one-half the height of the teeth. More deflection may be provided in some embodiments, for example, if the first and second members 278, 280 are at least partially in the same transverse plane prior to being engaged. As such members come into engagement, a greater degree of deflection may be provided. In some embodiments, less deflection may be suitable, such as where the other components of the system have substantially tight tolerances and little deformation upon deflection. As discussed above, the first and second members 278, 280 have sufficient resilience such that when peaks of the teeth of the first member 278 are circumferentially aligned with valleys between the teeth of the second member 280, the second ends 250, 252 of the first and second members 278, 280 move axially toward each other by about the same amount that the first and second members 278, 280 are deflected by the teeth.

As illustrated in FIG. 4, in some embodiments, the connector 270 can have a tubular structure 292 that extends from a first end 254 to a second end 258. The tubular structure 292 can have a consistent or variable diameter. A protrusion or shoulder 288 can be circumferentially positioned around the tubular structure 292 between the first and second ends 254, 258. In some embodiments, the pin 240 can pass through a portion of the shoulder 288. A portion of the tubular structure 292 can extend from the shoulder 288 to the first end 254 of the connector 270. An inflow component can be slid in an axial direction from the first end 254 to the second end 258. The inflow component can be slid over the tubular structure 292 until an end of the inflow component abuts with the shoulder 288. Further discussion of methods of coupling these structures are discussed below in connection with FIGS. 9A-9F and 12A-12F.

As discussed above, and illustrated in FIG. 4, the connector 270 can be provided with engagement features to ensure a secure connection with the inner surface of a graft or other inflow component. For example, the tubular structure 292 can have one or more engagement features 290, such as, for example, ribs, barbs, or a combination thereof. In some embodiments, the engagement features 290 are inclined toward the first end 254 of the connector 270 such that a proximal ridge is presented to engage the inner surface of the outflow component. The engagement features 290 can be positioned circumferentially around the tubular structure 292 and have a conical shape. The diameters of sides of the engagement features 290 facing one end of the connector 270 can be greater than the diameters of the sides facing an opposite end of the connector 270. In some embodiments, the one or more engagement features 290 are of equivalent diameters. In other embodiments, the engagement features 290 can increase in diameter towards one end of the connector 270, such as the second end 258.

In some embodiments, as illustrated in FIG. 4, the connecting device 266 can have proximally extending shrouds 284, 286. Inner surfaces of the shrouds 284, 286 can be provided with engagement features 294 that can include protrusions, channels, ribs, or combinations thereof. These engagement features 294 can also assist in ensuring a secure connection between an outer surface of a graft and the connector 270. These engagement features also reduce the surface area of material being compressed as the first and second members 278, 280 are engaged to help reduce the force required to be applied to the mechanism for a given amount of compression of (or pressure on) the graft material. When used in a surgery to apply a system like the vascular access system 50, reduced manual force to connect the components reduces fatigue for the surgeon, which can benefit the patient, the surgeon, and make the procedure simpler. In some embodiments, a space or gap is provided between the shrouds 284, 286 when an outer surface of a graft that is secured to the connector 270 when the connecting device is in a closed, secured, or locked configuration. The size of the gap or space between the shrouds 284, 286 can depend on the relative position of the first and second members 278, 280. The gap or space can thus be selected or customized to the thickness of a particular inflow component, e.g., graft. A thicker graft will be accommodated within the shrouds 284, 286 when a larger gap is provided therebetween in a closed or locked configuration of the connector 270, and a thinner graft can be accommodated within the shrouds when a smaller gap (or no gap) is provided therebetween in a closed or locked configuration.

In the illustrated embodiment, the shrouds 284, 286 have a semi-cylindrical configuration and extend axially between an end of the first and second members 278, 280 facing the end 254 of the connector 270 and the end 254. The shrouds 284, 286 can extend in an arcuate path along a portion of first and second members 278, 280 and rotate together with the first and second members when they move between open and closed configurations. In some embodiments, the shrouds 284, 286 can be omitted and/or substantially reduced in length.

In some embodiments, a further safety mechanism can be provided on the first and second members 278, 280 to ensure sufficient engagement of the gripping structures 296, 298. As shown in FIG. 2, protrusions 172 and 174 can be located at second ends of the first and second members. These protrusions 172, 174 are the first structures on the first and second members 278, 280 to come into contact with each other. The protrusions 172, 174 deflect the second ends 250, 252 of the first and second members 278, 280 apart and hold the first and second members apart after initial engagement of the second ends until the second ends slide past each other and overlap each other by a minimum amount before the teeth 296, 298 (or other engagement feature) come into engagement. In some embodiments, the first and second members can be held apart by the protrusions 172, 174 until the gripping structures or teeth move past each other at least a minimum number of teeth, such as, for example, at least two teeth. These protrusions may also serve as pry points if the connection is intended to be capable of being undone.

Figure 5:
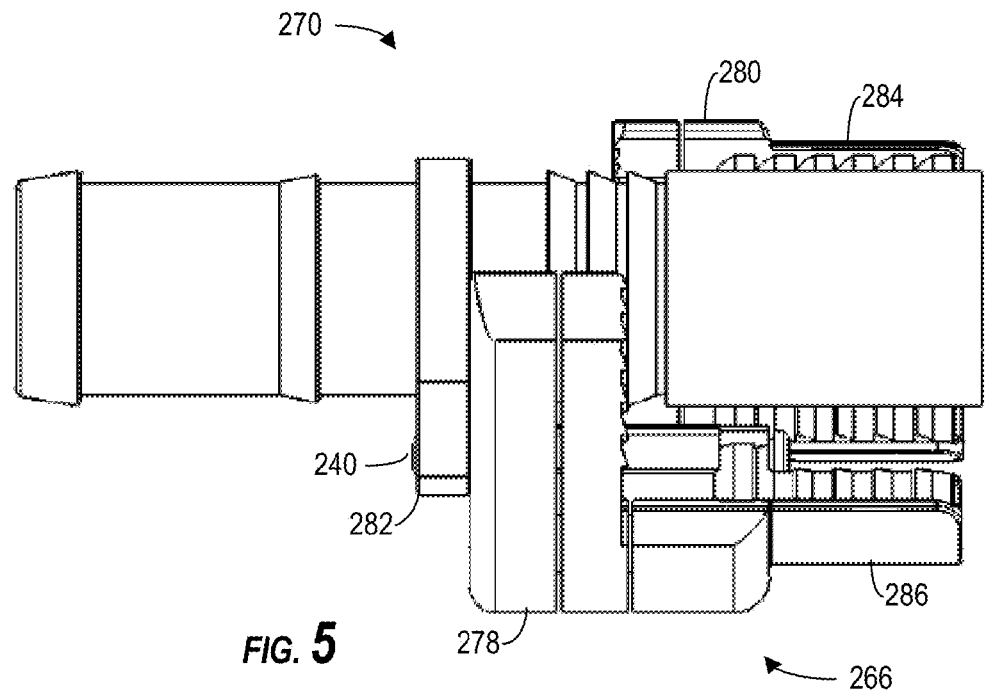
FIG. 5 is an end view of an embodiment of a connector taken at 4-4 of FIG. 3 in an open configuration.
Figure 6:
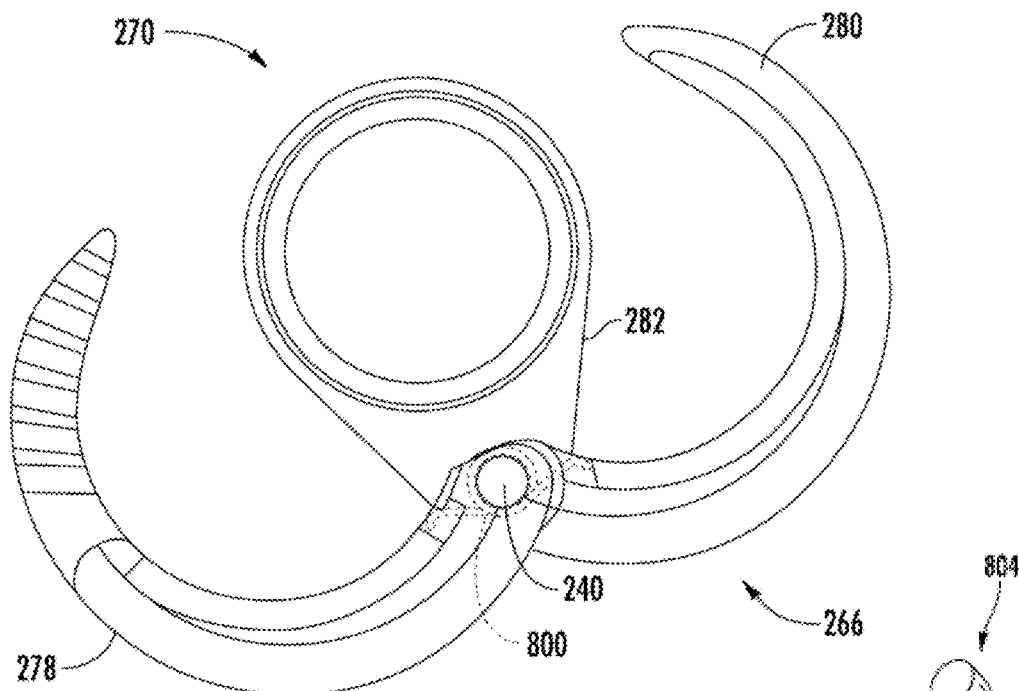
FIG. 6 is a plan view of an embodiment of a connector in an open configuration.

FIGS. 5 and 6 illustrate a plan view and an end view, respectively, of an embodiment of the connector 270. In the end view, an open position of the connecting device 266 is shown. This view also illustrates the arcuate shape, e.g., semi-circular configuration of the first and second members 278, 280. FIGS. 5 and 6 show, in particular, the first and second members 278, 280 pivotably connected at a hinge structure, such as pin 240, of flange 282 with shrouds 284, 286 extending out from surfaces of the first and second members.

Figure 6A:
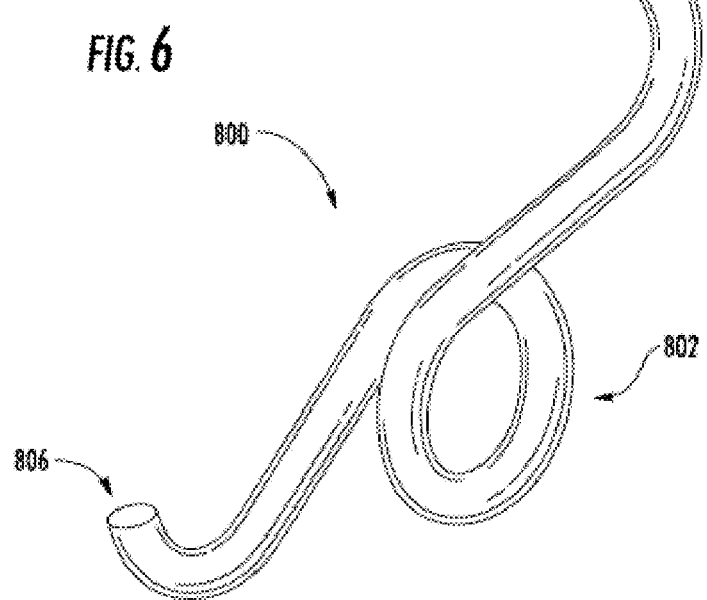
FIG. 6A is a perspective view of an embodiment of a spring structure.

FIGS. 6 and 6A illustrates an example spring 800 that may be positioned about the hinge of the connector 270. For example, the center portion of the spring 800 may include a coil 802. In some embodiments, the coil 802 may be positioned around the pin 240 of the hinge. In one embodiment, end portions 804, 806 of the spring 800 may engage the first and second members 778, 780, respectively, of the connector 270. That is, in some instances, the spring 800 may be configured to maintain the connector 270 in the open configuration as depicted in FIG. 6. In other instances, the spring 800 can be configured to apply a constant force between the teeth 296, 298 formed along the arcuate body of the first and second members 278, 280 when the connector 270 is in the closed configuration. The constant force between the teeth 296, 298 can provide a secured or locked engagement when the connector 270 is in the closed configuration.

FIG. 7 illustrates one embodiment of the strain relief structure 164 discussed above. A distal portion 140 of the strain relief structure 164, which has an elastomeric configuration, can include a cylindrical ring of silicones or polyurethanes. In one embodiment, the silicone can have a hardness of approximately 50 durometer (Shore A). Further details of the elastomeric configuration are discussed above. A proximal portion 142 of the strain relief structure 164 can comprise a resilient structure, such as a nitinol coil defining a lumen therein of substantially constant diameter. Other materials that can be used include PEEK, stainless steel, MP35N and other similar metals. As discussed above, a sleeve, such as silicone, can be disposed within the strain relief structure 164, which may have an outer diameter substantially the same as the inner diameter of the coil. In some embodiments, as discussed below with reference to FIG. 11, the sleeve may extend beyond the distal end of the coil. The coil preferably is wound sufficiently tightly such that adjacent turns of the wires touch each other. This structure substantially prevents compression of the coil, which during implantation, substantially prevents tissue from being caught between adjacent turns of the coil or prevents the tissue from compressing the coil axially. The strain relief structure 164 can have a length 144 of increasing diameter. The increasing diameter length 144 can enable this portion of the strain relief structure 164 to be positioned over the tubular structure 292 of the connector 270. In one embodiment, the sleeve disposed in the strain relief structure 164 also has an increasing inner diameter to accommodate the tubular structure 292 of the connector 270 as well as the inflow component. In another embodiment, the sleeve may include a constant diameter, which may be clamped within a portion of the connecting device 266.

FIGS. 8A-8C illustrate alternative embodiments of a connecting device. FIG. 8A illustrates an embodiment of a connecting device 410 in which a simple longitudinal sliding action firmly secures any graft or other inflow component (not shown) to a connector 414.

The connecting device 410 includes an outer ring 418 and an inner force applying member 422. The inner force applying member 422 can be a collet in one embodiment. The force applying member 422 can include multiple fingers 426 that engage a portion of the underlying graft or other inflow component. Initially the fingers 426 are in an open position or configuration (as shown) to allow insertion of the inflow component. The inflow component may be a tubular body with an inner circumference larger than a proximal end 430 of the connector 414 and an outer circumference less than the relaxed inner circumference of the force applying member 422. The graft or inflow component can be slid distally over the proximal end 430 of the connector 414. In one embodiment a central flange 434 is provided on the connector 414. A confirmation of proper placement of the inflow component is provided by configuring the flange 434 with an outer circumference greater than at least the inner circumference of the inflow conduit such that the inflow conduit can be butted up to the central flange 434. In one method of connection, relative distal motion of the inflow component over the proximal end 430 is provided until the distal end of the inflow component is pushed up against the flange 434.

The outer ring 418 is configured to anchor or secure the inflow component to the connector 414. For example, the outer ring 418 can be advanced proximally relative to the force applying member 422 toward the end of the fingers 426. In FIG. 8A, a plurality of fingers 426 are disposed about the proximal perimeter of the force applying member 422. The fingers 426 are shown toward the upper right in FIG. 8A. One configuration for securing the inflow component between the force applying member 422 and the connector 414 is to provide a tapered interface between the outer ring 418 and fingers 426 or between the outer ring 418 and the connector 414. The tapered interface could be inclined in the proximal direction to progressively larger diameter, width or circumference to provide a progressively greater friction force between the force applying member 422 and the inflow component. The increasing force can also be applied by this technique between the inflow conduit and the connector 414 proximal of the flange. These forces cause the force applying member 422 to grip and secure the inflow conduit to the connector.

By providing a suitable taper, the point of initial engagement is permitted to vary depending on the wall thickness of the underlying graft or other inflow component. The design above utilizes friction between the outer ring 418 and force applying member 422 to maintain an engaged configuration. In certain embodiments, the tapered surface and axial or longitudinal movement can be replaced with or supplemented by threads, a latch, a spring mechanism, or a combination thereof.

The underlying connector 414 can be titanium or other strong and well machineable material. If the force applying member 422 is a collet, it can be formed of a spring metal or polymer with sufficient flexibility. Flexibility is desired to allow the fingers to deflect without too high of force. Possible materials for the collet include PEEK, polytheylenes, and other polymers. Metals with such as nitinol or stainless steel may be suitable. The material may be designed to yield or not depending on the thickness of the fingers. The outer ring 418 may be any material with high enough strength to maintain a small profile (thin wall). Some consideration for friction may be given with the underlying collet interface depending on ease of activation and resistance to sliding post connection desired.

FIG. 8B illustrates another embodiment having a hinge-type configured mechanism or connecting device 500. One example of a hinge-type mechanism is a clamshell. In this design, a plurality of overlapping fingers 510 is provided to engage portions of an outer surface of the inflow component. For example, two fingers 510A, 510B can be provided where each overlaps approximately one-half of a short distal length of an outer surface of the inflow component, which is disposed between the fingers and the connector 514. Initially the fingers 510A, 510B are in an open position or configuration. Thereafter, they are moved to a closed configuration, as shown in FIG. 8B. In the open configuration, the inflow component can be advanced up to the flange 534, as discussed above. Thereafter, the fingers 510A, 510B can be brought together to apply a compression force onto the distal length of the inflow component disposed between the finger 510A, 510B and the body of the connector 514. In some embodiments, the fingers 510A, 510B move past, overlap, and/or slide past each other in order to engage each other and/or the inflow component in a closed configuration. In particular, the graft (or other inflow component) is slid on, then confirmed to be butted up to the central flange 534, and the fingers 510A, 510B pinched together to close and engage the graft. The point of initial engagement varies depending on the wall thickness of the underlying graft. A range of positions of the fingers 510A, 510B providing sufficient securement is provided such that a range of thicknesses and compressibility of the inflow component can be accepted. The fingers can include teeth 524 or other gripping structures on mating faces that provide for a positive lock and maintain the force upon the graft (within one tooth) that was provided. The teeth 524 can be formed in an arcuate path and slide past each other to come to a secured engagement at any position over the arcuate path.

The underlying connector component can be formed as discussed above. The fingers 510A, 510B may be a metal or polymer with the tradeoff between strength and flexibility. Flexibility is desired to allow the teeth to slip past each other without too high of force. Strength is required to maintain engagement and not strip the teeth. PEEK may be a suitable material.

In the illustrated embodiment, the teeth 510A, 510B are pivotably connected to the flange 534 at an axis of rotation. A pin 518 can be provided for such pivotable motion.

FIG. 8B illustrates that in some embodiment, other hinge-type connector devices can be configured without a shroud. This can result in ease of and less costly manufacturing. In some embodiments, the connector device as illustrated in FIG. 8B, can be combined with the strain relief structure 164 as described above.

FIG. 8C illustrates an embodiment of a connecting device 600 in which a member 610 has a free state for clamping an inflow component to the connector 614. In particular, the member 610 can be a sprung member configured to move toward a smaller circumference or pinching configuration when released. In one form, the member 610 includes two U-shaped halves (in cross-section) that each engage a portion of the underlying graft. The natural state for the sprung member is in the closed position (as shown). During installation of the graft, the side opposite the U members (left end in FIG. above) is pinched. This pinching action causes the member to deform and the U members to separate and allow insertion of the graft material or other inflow component.

While remaining pinched at the distal end, the graft or other inflow component can be slid distally then confirmed to be butted up to the central flange similar to the techniques discussed above. Thereafter, the member 610 can be released at the distal end. The natural state of the member forces U shaped halves inward at the proximal end and together to close and engage the graft. The point of initial engagement varies depending on the wall thickness of the underlying graft. The design above is shown with an outer clear polymer sleeve 618 that may be beneficial for biocompatibility or ergonomics.

The underlying connector component may be preferably titanium or other strong and well machineable material. The sprung member may be spring metal or polymer with a requirement being flexibility and resistance to yielding. Possible materials for the sprung member include nitinol, spring stainless steels, and possibly polymers. The outer sleeve (if provided) may be constructed of silicone, polyurethane, or other materials disclosed herein or otherwise known in the art.

Although the foregoing connecting device can secure an inflow component to the connector 614, additional barbs may be provided to increase retention force of the graft or inflow component. These may be on the underlying portion of the connector (to engage ID of graft), or on the other portions, e.g., on the U spring members, fingers, or collet fingers (to engage the OD of graft).

The nominal inner diameter of the above devices may be adapted and suitable for use with any graft or inflow component used for vascular access. Examples include 6 mm ID grafts as well as 5 and 7 mm ID grafts.

Radiopaque materials may be included within the connector devices described herein. Examples of suitable material include but are not limited to: platinum, tantalum, tungsten, gold, palladium, iridium, barium sulfate, and any combination thereof. These marking materials may be doped into the molded materials or in the form of rings, patches, plates, wire, or other shapes 149 as illustrated in FIG. 1. They may be distributed in the entire device or at one or both ends of the device or anywhere in between.

In some instances, a kit for accessing blood from a patient's vasculature can be provided that can include, among other things, one or more of the components disclosed herein. For example, the kit can include an outflow component connector for interconnecting the inflow and outflow components, a connecting device, and a dilator to assist in expanding an inflow component for attachment to the connector. Other components may be included in the kit. The kit may be sterilized.

FIGS. 9A-9F illustrate one embodiment of attaching an inflow component 362 to a first end 354 of a connector 370. A second end 358 of the connector 370 can be configured to be connected to an outflow component (schematically shown in FIG. 1). FIG. 9A illustrates an initial step of placing the strain relief structure 364 over the inflow component 362. The arrow A illustrates one technique in which a proximal portion 342 which can include a coil is advanced over a distal portion 361 of the inflow component 362. Preferably a distal portion 340 of the strain relief structure 364 is moved to a location proximal of the distal portion 361 of the inflow component 362.

The inner diameter or perimeter of the inflow component 362 can match or be substantially equivalent to the outer diameter or perimeter of the connector 370. FIG. 9B illustrates that a dilator 302 can be used to radially expand one end of the inflow component 362, e.g., the distal portion 361 thereof. The radial expansion may be due primarily to elastic deformation. The dilator 302 includes a distal zone 302A that is configured for gripping by the user and a proximal zone 302B that is configured for insertion into the inflow component 362. The proximal zone 302B is tapered to facilitate easy insertion of the dilator 302 into the inflow component 362. The tapered feature of the proximal portion 302B also ensures gradual enlargement of the lumen of the inflow component 362 to a size that will provide a good connection to the connector, as discussed further below. The dilator 302 preferably also includes a depth limiter 302C, which can be configured as a shoulder. The depth limiter 302C prevents over-insertion of the dilator 302 into the inflow component 362, which could cause over-enlargement of the inflow component 362. Over enlargement can compromise the security of the connection to the connector, as discussed below.

FIG. 9B illustrates the use of the dilator by arrows B1 and B2. B1 illustrates that the dilator is first inserted into the lumen of the inflow component 362 up to the depth limiter 302C. B2 illustrates that the dilator 302 is then removed from the inflow component 362, providing suitable size and shape of the distal portion 361 thereof. In a preferred embodiment, the dilator 302, at least on the outer surface of the proximal zone 302B, is formed of a highly lubricious material, such as polytetrafluoroethylene (PTFE), which has been found to significantly facilitate the dilation process.

FIG. 9C illustrates that after the inflow component 362 has been dilated, it can be slid in the direction of the arrow C over the first end 354 of the connector 370 in an axial direction towards the second end 358. The size and shape provided by the dilator 302 preferably is one that provides a tight fit, e.g., an interference fit, between the inflow component 362 and the first end 354 of the connector 370. In some grafts, the inflow component 362 will respond to the dilating process illustrated in FIG. 9B by at least some elastic recoil or recovery, which provides at least a partial seal between the inflow component 362 and the first end 354 of the connector 370. In other embodiments, a seal can be imposed between these structures by a clamping structure, such as by closing the clam shell members discussed above. The inflow component 362 can be slid axially until one end thereof abuts with a shoulder 388. Engagement features 390 similar to those discussed above in connection with the connector 270 can be positioned on an outer surface of the connector 370 to mechanically engage with the inner surface or engagement features (not shown) positioned on an inner surface of the inflow component 362.

In some embodiments, first and second members 378, 380 of the connecting device 366 can then be actuated, e.g., pinched or pushed together, such that the gripping structures or teeth 396, 398 on respective mating surfaces of the first and second members 378, 380 engage with each other. This is illustrated by the arrows D in FIG. 9D. Portions of the first and second members 378, 380 can be moved past, slid past or overlapped with each other until a closed configuration and secure connection between the inflow component 362 and connector 370 is realized. A safety structure can be provided on the connector 370 to require at least a minimal actuation to ensure sufficient amount of engagement between the engagement features on the first and second members 378, 380. Surfaces 384, 386 of the connecting device can also have engagement features 394 positioned on an inner surface to provide further mechanical engagement with the outer surface of the inflow component 362.

As illustrated in FIG. 9E, there can be a gap or space 400 between ends of shrouds 384, 386 when the connecting device is in a closed configuration or position. The gap or space 400 may be larger or smaller depending on characteristics, such as wall thickness, of the inflow component 362. In some embodiments, the shrouds 384, 386 can have edges 402, 404 that extend longitudinally in a direction parallel to a longitudinal axis of the connector 370. The gap 400 can extend circumferentially between the two edges 402, 404 when the connecting device is in a closed configuration.

FIG. 9F illustrates one embodiment of installing a strain relief structure 364 over a proximal end 314 of the connecting device 366. In one technique, a friction fit is formed between the strain relief structure 364 and the connecting device 366 and a slip fit between the strain relief structure 364 and the inflow component 362 for strain relief. The strain relief structure 364 helps prevent kinking or collapsing of the inflow component 362 as it extends from the connecting device 366. The strain relief structure 364 can be slid, as illustrated by the arrow F, over a distal section of inflow component 362 toward the distal end thereof, which is secured to the connecting device 366 in a closed configuration. This sliding motion is in a direction towards second end 358, and continues until it reaches the proximal end 314 of the connecting device 366. For example, a distal end of the strain relief structure, such as an elastic sleeve, can be slid over the outer surfaces of shrouds 384, 386 of the connecting device 366 to form a friction fit thereon.

Figure 10:
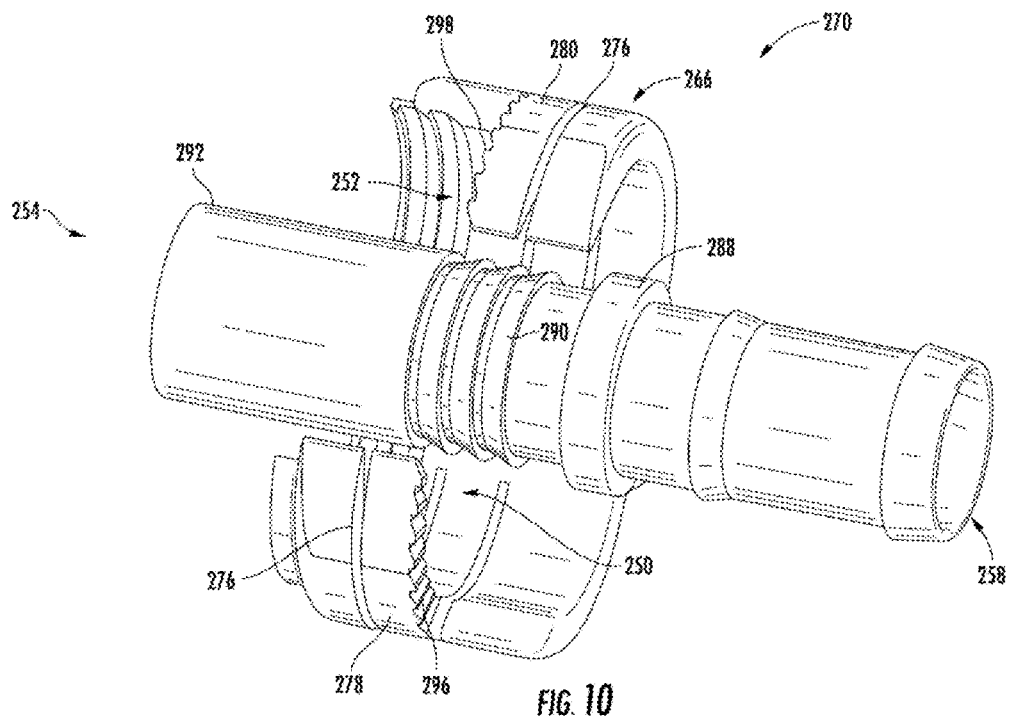
FIG. 10 is a perspective view of an embodiment of a connector in an open configuration.

FIG. 10 illustrates another embodiment of the connector 270 in an open configuration. In the embodiment of the connector 270 as depicted in FIG. 10, the shrouds 284, 286 are omitted or otherwise substantially reduced as compared to the embodiment of the connector 270 depicted in FIG. 4. For example, in some instances, the connector 270 generally does not include proximally extending shrouds that extend out from a side of the first and second members 278, 280 towards a first end 254 of the connector 270. In other instances, however, the connector 270 may include proximally extending shrouds that slightly extend out from a side of the first and second members 278, 280 towards the first end 254 of the connector 270. That is, the shrouds may only partially extend out from a side of the first and second members 278, 280 towards the first end 254 of the connector 270, but may not extend all the way to the first end 254 of the connector 270.

Still referring to FIG. 10, in one embodiment, the first and second members 278, 280 of the connecting device 266 are configured to engage portions of an outer surface of a distally extending sleeve of a strain relieve device positioned about an inflow component or graft (not shown) to secure it to the connector 270. A range of positions or closed configurations for the first and second members 278, 280 are provided such that a range of thicknesses of sleeves or grafts can be secured to the connector 270. In some embodiments, the second ends 250, 252 of the first and/or second members 278, 280 of the connecting device 266 can be provided with protrusions or gripping structures, such as teeth 296, 298, on mating surfaces that maintain compressive force on the sleeve and/or graft when the connector is in the closed configurations. The teeth 296, 298 can be formed along an arcuate body on the first and second members 278, 280, allowing a secured or locked engagement at any position over an arcuate path of movement of the first and second members 278, 280. In some instances, the first ends 246, 248 of the first and second members 278, 280 can be pivotably connected at one axis of rotation.

In some embodiments, to facilitate engagement of the teeth 296, 298 some axial displacement of at least a portion of at least one of the first and second members 278, 280 can be provided. For example, the slot 276 can enable the second ends 250, 252 of the first and second members 278, 280 to deflect away from each other by an amount sufficient to enable the teeth to slide past each other when so deflected. In some embodiments, the connector 270 can have a tubular structure 292 that extends from a first end 254 to a second end 258. The tubular structure 292 can have a consistent or variable diameter. A protrusion or shoulder 288 can be circumferentially positioned around the tubular structure 292 between the first and second ends 254, 258. In some embodiments, the pin 240 (see FIG. 5) can pass through a portion of the shoulder 288. A portion of the tubular structure 292 can extend from the shoulder 288 to the first end 254 of the connector 270. An inflow component can be slid in an axial direction from the first end 254 to the second end 258. The inflow component can be slid over the tubular structure 292 until an end of the inflow component abuts with the shoulder 288. Similarly, a sleeve component of a strain relieve device can be slid in an axial direction from the first end 254 to the second end 258. The sleeve can be slid over the tubular structure 292 and/or the inflow component until an end of the sleeve abuts with the shoulder 288. Further discussion of methods of coupling these structures are discussed below in connection with FIGS. 12A-12F.

The connector 270 can be provided with engagement features to ensure a secure connection with the inner surface of a graft or other inflow component. For example, the tubular structure 292 can have one or more engagement features 290, such as, for example, ribs, barbs, or a combination thereof.

FIG. 11 illustrates one embodiment of the strain relief structure 164 for surrounding an inflow component or an outflow component. A distal portion 140 of the strain relief structure 164 can include a sleeve 146 extending therefrom. That is, in some embodiments, the sleeve 146 may extend beyond the distal end of the coil. In some instance, the sleeve 146 can be disposed at least partially within the strain relief structure 164, which may have an outer diameter substantially the same as the inner diameter of the coil. In other instances, the sleeve 146 may not be disposed within the strain relief structure 164 and may only extend from the coil. In some embodiments, the sleeve may be silicone. A proximal portion 142 of the strain relief structure 164 can comprise a resilient structure, such as a nitinol coil, defining a lumen therein of substantially constant diameter. In some embodiments, the strain relief structure 164 can have a length 144 of increasing diameter. The increasing diameter length 144 can enable this portion of the strain relief structure 164 to be positioned over the tubular structure 292 of the connector 270. In one embodiment, the sleeve disposed within the strain relief structure 164 can also have an increasing inner diameter to accommodate the tubular structure 292 of the connector 270 as well as the inflow component. In another embodiment, the sleeve may include a constant diameter. The strain relief structure 164 reduces or minimizes kinking or pinching of the inflow component 162.

Figure 12A:
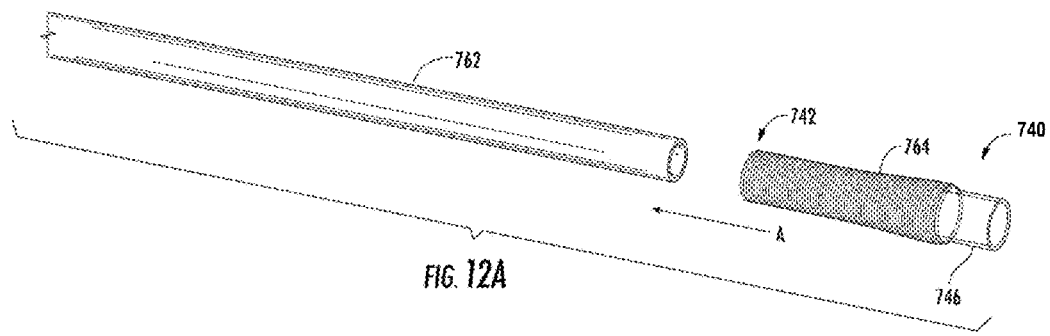
FIGS. 12A-12F illustrate example systems and method for facilitating a connection.

FIGS. 12A-12F illustrate one embodiment of attaching an inflow component 762 to a first end 754 of a connector 770. A second end 758 of the connector 770 can be configured to be connected to an outflow component. FIG. 12A illustrates an initial step of placing the strain relief structure 764 over the inflow component 762. The arrow A illustrates one technique in which a proximal portion 742, which can include a coil and an inner sleeve 146, is advanced over a distal portion of the inflow component. Preferably a distal portion 740 of the strain relief structure 764 is moved to a location proximal of the distal end of the inflow component 762.

Figure 12B:
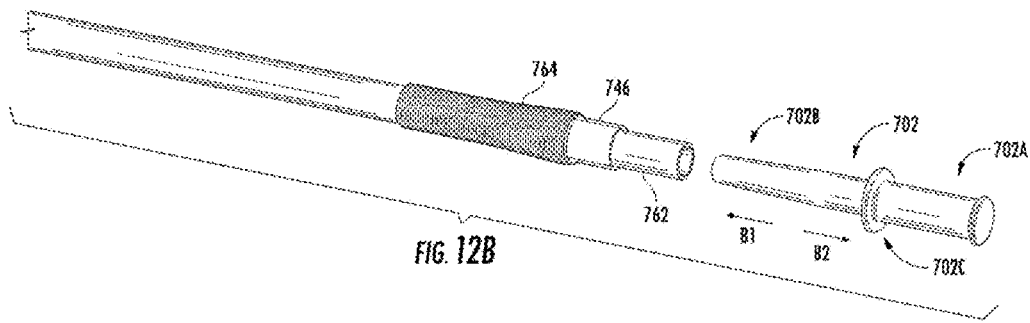

The inner diameter or perimeter of the inflow component 762 can match or be substantially equivalent to the outer diameter or perimeter of the connector 770. In some instances, it is advantageous to have the inner diameter of the inflow component 762 match or be almost the same as the inner diameter of the connector 770 to keep the inner profile as smooth as possible between the two components. In such instances, this may require the use of the dilator (discussed below) or other means for stretching an end of the inflow component 762. Moreover, the inner diameter or perimeter of the sleeve 746 can match or be substantially equivalent to the outer diameter or perimeter of the inflow component 762. FIG. 12B illustrates that a dilator 702 can be used to radially expand one end of the inflow component 762, e.g., the distal end thereof. The dilator 702 includes a distal zone 702A that is configured for gripping by the user and a proximal zone 702B that is configured for insertion into the inflow component 762. The proximal zone 702B is tapered to facilitate easy insertion of the dilator 702 into the inflow component 762. The tapered feature of the proximal portion 702B also ensures gradual enlargement of the lumen of the inflow component 762 to a size that will provide a good connection to the connector 770. The dilator 702 preferably also includes a depth limiter 702C, which can be configured as a shoulder.

FIG. 12B illustrates the use of the dilator by arrows B1 and B2. B1 illustrates that the dilator is first inserted into the lumen of the inflow component 762 up to the depth limiter 702C. B2 illustrates that the dilator 702 is then removed from the inflow component 762, providing suitable size and shape of the distal end thereof. With at least the ePTFE based grafts, it may be beneficial to dilate to a larger diameter than the outer diameter of the connector to account for recoil. Also, recoil is a time dependent function and, therefore, may be enable the dilated portion of the graft to initially be easily slid on the connector; the dilated portion may then tighten down to some level. In one example embodiment, the outer diameter of the dilator may be 0.265" and the outer diameter of connector may be 0.236" at the peak of barbs. Dilators with smaller outer diameters may result in interference (i.e., less than 0.236" graft inner diameter) before the graft is positioned over the connector. Even the 0.236" can have slight interference. In some instances, interference may be tolerated as long as it does not become too difficult to advance the graft over the connector. Sometimes a second dilation is beneficial.

Figure 12C:
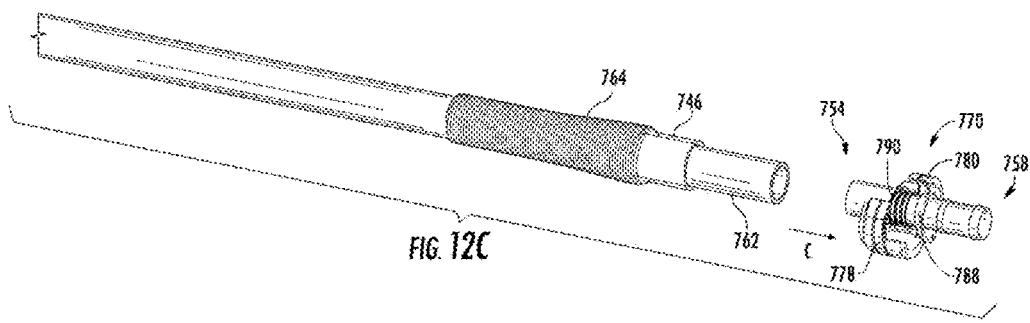

FIG. 12C illustrates that after the inflow component 762 has been dilated, it can be slid in the direction of the arrow C over the first end 754 of the connector 770 in an axial direction towards the second end 758. The size and shape provided by the dilator 702 preferably is one that provides a tight fit, e.g., a slight interference fit, between the inflow component 762 and the first end 754 of the connector 770. The inflow component 762 can be slid axially until one end thereof abuts with a shoulder 788. Engagement features 790 similar to those discussed above in connection with the connector 770 can be positioned on an outer surface of the connector 770 to mechanically engage with the inner surface or engagement features (not shown) positioned on an inner surface of the inflow component 762. Also, the material of the dilator may have an effect on certain grafts, such as for example non ePTFE grafts. For example, certain grafts will not slide over other plastics with higher coefficients of friction but will slide over the PTFE material dilator. Since ePTFE grafts are inherently lubricious themselves, the material of the dilator may be less important for them.

Figure 12D:
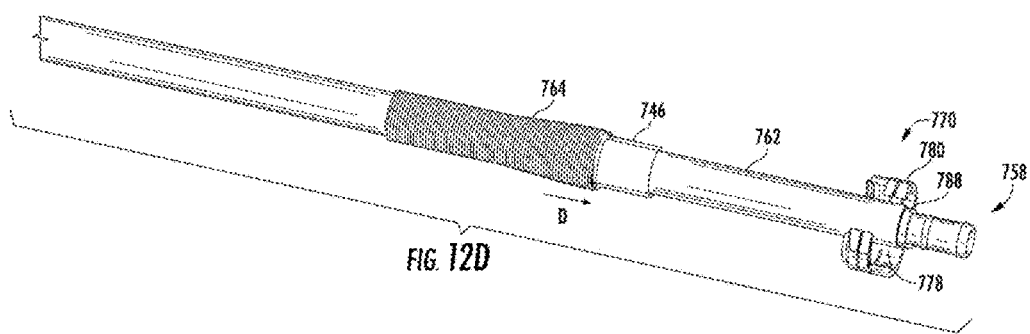
Figure 12E:
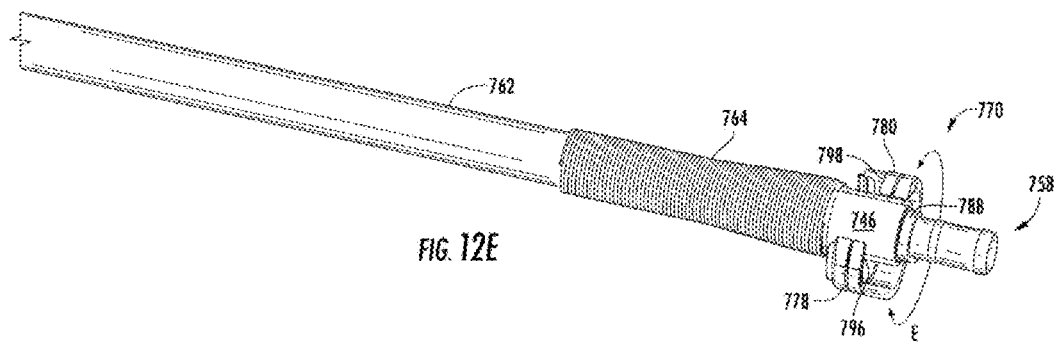

FIGS. 12D and 12E illustrate that after the inflow component 762 is slid over the first end 754 of the connector 770 to abut with the shoulder 788, the strain relief structure 764 can also be slid axially (in the direction of arrow D) over the first end 754 of the connector 770. That is, the strain relief structure 764 can be slid axially over the inflow component 762 towards the second end 758 until the distal end of the sleeve 746 abuts with the shoulder 788. In this manner, the sleeve 746 may be positioned within the connector 770.

In some embodiments, first and second members 778, 780 of the connector 770 can then be actuated, e.g., pinched or pushed together, such that the gripping structures or teeth 796, 798 on respective mating surfaces of the first and second members 778, 780 engage with each other. This is illustrated by the arrows E in FIG. 12E. Portions of the first and second members 778, 780 can be moved past, slid past, or overlapped with each other until a closed configuration and secure connection between the inflow component 762, the strain relief structure 764, and the connector 770 is realized.

Figure 12F:
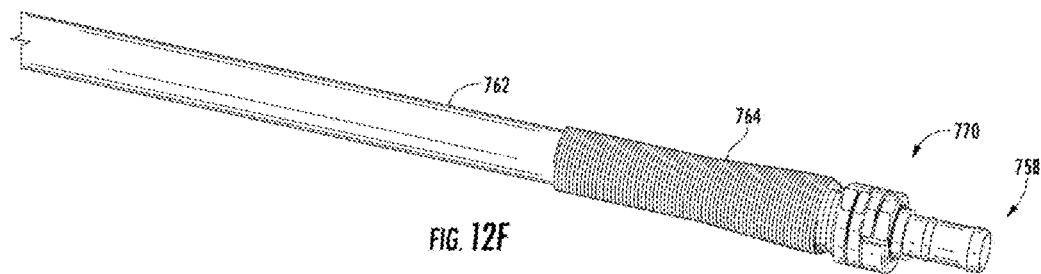

FIG. 12F illustrates one embodiment of installing a strain relief structure 764 over a proximal end 754 of the connecting device 766. In one technique, at least a portion of the sleeve 746 of the strain relief structure 764, along with at least a portion of the inflow component 762 may be clamped, pinched, locked, or a combination thereof by the first and second members 778, 780 of the connector 770. That is, the sleeve 746 may be secured within the connective device 766 by the first and second members 778, 780 and/or by the shrouds 284, 286 (see FIG. 4) if present.

As discussed above, the aforementioned embodiments allow the user (e.g., a surgeon) to utilize a standardized outflow component and connector system with any commonly available graft or inflow component of their choosing. This will allow surgeons to use grafts they have the most experience with and developed implantation skills for.

Another advantage is allowing a standardized outflow component and connector system to be used with grafts capable of being accessed either early or instantly. This eliminates the need for a temporary dialysis catheter while the graft is incorporating into the body. This enhancement reduces the risk of infection with temporary dialysis catheters, which are common and costly in hemodialysis. Some examples of such structures are discussed in US 2007/0167901A1, which was published on Jul. 19, 2007, which is hereby incorporated by reference.

The foregoing method of connecting an inflow component to any of the connectors herein can be embedded within a broader method of applying such a device to a patient. Such a method can involve accessing a vein in the patient into which an outflow component is to be inserted. For example, a jugular vein could be accessed in such a method. The distal end of the outflow component can be positioned distant from the access site, e.g., at any location between the access site to a chamber of the heart.

The proximal end of the outflow component can thereafter be positioned at any suitable anatomical location, e.g., at the nearest delta-pectoral groove. Such positioning of the proximal end of the outflow component can be achieved in any suitable manner, such as by tunneling subcutaneously the proximal end from adjacent to the venous insertion site to adjacent to the delta-pectoral groove.

The broader method can also include coupling the proximal end of an inflow component with a vascular segment different from the insertion site, which can be a jugular vein. The inflow component can be coupled with a different vascular segment, e.g., a brachial artery by any suitable technique. One technique involves suturing the proximal end to the artery, for example producing an end-to-side anastomosis. Attachment of the proximal end of the inflow component can be performed through a second incision formed through the skin adjacent to the vascular segment to which the inflow component is to be connected. After connecting the inflow component, the distal end of the inflow component can be tunneled, e.g., subcutaneously to an anatomical location suitable for coupling to the outflow component, e.g., to the delta-pectoral groove, where a third incision can be formed.

Once distal and proximal portions of the inflow and outflow components respectively are located at a connection zone (e.g., delta-pectoral groove), connection of these components can be achieved using the connector systems and methods discussed above. In one convenient technique, a short length of a distal portion of the inflow component is lifted out of the patient through the third incision and a short length of a proximal portion of the outflow component is lifted out of the patient through the third incision. The proximal end of the outflow component is advanced over the distal tubular structure of the connector including the engagement features 168 (or similar, as discussed herein). The distal end of the inflow component is advanced over the proximal tubular structure of the connector. If present, the shrouds are closed around a length of the sleeve and/or inflow component extending proximally from the distal end thereof, as discussed above. A variety of methods of this type are discussed in general in U.S. Pat. No. 7,762,977, which is hereby incorporated by reference herein for the purpose of elaborating on these techniques, and for all other purposes.

The foregoing devices and variants thereof enable the provision of a vascular access system. The inflow component can be attached by any means to an artery by suturing or otherwise arterialized. In other embodiments, the proximal end of the inflow component is attached by an expandable member, which can be self-expanding or balloon expandable. A self-expanding version can include a sinusoidal circumferential member adapted to be enlarged to at least the inner size of the artery. This enlargement enables a proximal portion of the inflow conduit to expand toward the inner wall of the artery, e.g., to be pressed into engagement with an internal segment of an artery. Another technique for arterializing the inflow component involves providing a coupling structure, which can be one or more stent-like structures, as discussed in US 2009/0076587A1, published Mar. 19, 2009, which is incorporated by reference herein in its entirety. For example, at least a portion of the inflow component, e.g., including at least a portion of the coupling structure, can be deployed within the vessel and the remainder of the inflow component can extend from the vessel to the connector.

A portion of the outflow component is adapted to be inserted within a vein at an insertion site. The outflow component can have an outside diameter which is less than an inner diameter of the vein and can have at least one opening in an end thereof with at least one of the openings in the catheter section to be disposed distant from the insertion site. For example, an outlet can be in the heart.

In operation, blood flows from the artery through the catheter and is returned to the venous side of the circulatory system through an opening in the outflow component. The system preferably provides laminar blood flow between the artery and the vein. In certain applications, blood flows through the vein uninterrupted around at least an outer portion of the outflow component.

Access to the system can be provided in any suitable way, such as by providing a needle having a first end coupled to a hemodialysis device and having a second end adapted for insertion directly into the inflow component. Blood may thereby be shunted from the vascular access device to a dialysis device and back to the patient's circulatory system.

Although disclosed in the context of certain preferred embodiments and examples, it will be understood by those skilled in the art that the present disclosures extend beyond the specifically disclosed embodiments to other alternative embodiments and/or uses of and obvious modifications and equivalents thereof. In addition, while several variations have been shown and described in detail, other modifications, which are within the scope of these disclosures, will be readily apparent to those of skill in the art. It is also contemplated that various combinations or sub-combinations of the specific features and aspects of the embodiments may be made and still fall within the scope of the disclosures. It should be understood that various features and aspects of the disclosed embodiments can be combined with or substituted for one another in order to form varying modes of the disclosed embodiments. Thus, it is intended that the scope of at least some of the present embodiments herein disclosed should not be limited by the particular disclosed embodiments described above.

What is claimed is:

1. A system for providing continuous flow of blood between two locations in a cardiovascular system of a patient, comprising:
   a blood conduit having a distal portion and a proximal portion, the distal portion configured to be inserted into a blood vessel at an insertion site and to be advanced therethrough to a location spaced apart from the insertion site; and
   a connector comprising:
      a tubular body comprising a proximal portion and a distal portion, wherein the distal portion of the tubular body is configured to engage the proximal portion of the blood conduit, and wherein the proximal portion of the tubular body is configured to be inserted into an end of a vascular graft;
      a flange extending from the tubular body between the proximal portion of the tubular body and the distal portion of the tubular body; and
      a connecting device comprising first and second members pivotably connected together at one end by a hinge mechanism having one axis of rotation mounted to the flange, wherein the first and second members comprise an open configuration and a first closed configuration providing a first gap between an inner surface of the first and second members and an outer surface of the proximal portion of the tubular body and a second closed configuration providing a second gap between the inner surface of the first and second members and the outer surface of the proximal portion of the tubular body;
   wherein the first gap accommodates a first vascular graft having an inner perimeter matching the outer perimeter of the proximal portion of the tubular body and a first wall thickness and the second gap accommodates a second vascular graft having an inner perimeter matching the outer perimeter of the proximal portion of the tubular body and a second wall thickness different than the first wall thickness;
   whereby continuous flow is provided from grafts of different wall thicknesses through the connector and into the blood conduit.

2. The system of claim 1, wherein the first and second closed configurations are for securing fluid conduits of different sizes and the first and second members have second ends disposed away from the end pivotably connected to the flange.

3. The system of claim 2, wherein the first member has a plurality of notches formed on a surface of the first member adjacent to the second end of the first member, the second end of the second member being configured to engage the notches of the first member.

4. The system of claim 3, wherein the connector has a first configuration in which the second end of the second member engages a first range of notches, the connector also having a second configuration in which the second end of the second member engages a second range of notches including at least one notch between the first range of notches and the first end of the first member.

5. The system of claim 3, wherein the second member comprises a second plurality of notches formed on a surface of the second end of the second member configured to engage at least one notch of the plurality of notches of the first member.

6. A connector for implantation in a cardiovascular system, the connector comprising:
   a tubular body comprising a distal tubular body and a proximal tubular body;
   a flange extending from the tubular body between the proximal tubular body and distal tubular body; and
   a connecting device, comprising:
      a first member having a first end pivotably coupled with the flange, a second end disposed away from the first end of the first member, and a plurality of notches formed on a surface of the first member adjacent to the second end of the first member; and
      a second member having a first end pivotably coupled with the flange, a second end disposed away from the first end of the second member, and a second plurality of notches formed on a surface of the second end of the second member configured to engage at least one notch of the plurality of notches of the first member to secure an inflow component to the proximal tubular body,
   wherein the first end of the first member and the first end of the second member are pivotably connected together by a hinge mechanism having one axis of rotation mounted to the flange,
   wherein the connecting device comprises an open configuration and one or more closed configurations comprising a gap between an inner surface of the first and second members and an outer surface of the proximal tubular body.

7. The connector of claim 6, wherein the connecting device further comprises a plurality of closed configurations configured to secure inflow components of different sizes to the proximal tubular body.

8. The connector of claim 6, wherein the connective device has a first closed configuration in which the second end of the second member engages a first range of notches, the connecting device also having a second closed configuration in which the second end of the second member engages a second range of notches including at least one notch between the first range of notches and the first end of the first member.

9. The connector of claim 6, further comprising a spring disposed about the hinge mechanism, in communication with the first and second members, and configured to (i) maintain the connector in an open configuration, and/or (ii) apply a force between at least one notch of the plurality of notches of the first member and at least one notch of the plurality of notches of the second member when in a closed configuration.

10. The connector of claim 6, further comprising a plurality of engagement features disposed on an outer surface of the distal tubular body.

11. The connector of claim 6, further comprising a plurality of engagement features disposed on the outer surface of the proximal tubular body.

12. The connector of claim 6, further comprising shrouds extending out from a portion of each of the first and second members.

13. The connector of claim 12, further comprising a plurality of engagement features disposed on an inner surface of the shrouds.

14. The connector of claim 6, further comprising a first slot positioned adjacent to the second end of the first member, the first slot configured to enable the second end of the first member to deflect away from the second end of the second member by an amount sufficient to enable the first plurality of notches to slide past the second plurality of notches when so deflected.

15. The connector of claim 6, further comprising a second slot positioned adjacent to the second end of the second member, the second slot configured to enable the second end of the second member to deflect away from the second end of the first member by an amount sufficient to enable the second plurality of notches to slide past the first plurality of notches when so deflected.

16. The connector of claim 6, further comprising a strain relief structure configured to couple with an end of the connector to form a slip fit with the inflow component for providing strain relief to the inflow component.

17. The connector of claim 16, wherein the strain relief structure comprises an inner sleeve disposed about a distal end of the inflow component configured to be secured between the connecting device and the proximal tubular body.

18. The connector of claim 16, wherein the strain relief structure comprises an elastomeric distal portion and a resilient proximal portion, the elastomeric distal portion configured to elastically expand to receive at least a portion of the connecting device, the resilient proximal portion configured to reduce or minimize excessive narrowing of the inflow component at least adjacent to the proximal tubular body.

19. A method for coupling tubular segments in a cardiovascular system, the method comprising:
   radially expand an end of the inflow component with a tissue graft dilator;
   engaging the end of the inflow component with the connector of claim 6 such that a lumen of the connector is in fluid communication with a lumen of the inflow component; and
   actuating the connecting device from a disengaged configuration to an engaged configuration such that the inflow component is compressed by the connecting device.

20. The method of claim 19, further comprising:
   positioning a strain relief structure about the inflow component for providing strain relief to the inflow component; and
   coupling the strain relief structure with an end of the connector.

21. A connector for fluidly coupling proximal and distal tubular segments of a fluid conduit in a cardiovascular system, the connector comprising:
   a connector body comprising a proximal portion and a distal portion, wherein the connector body comprises an outer surface defining a first outer perimeter and an inner surface defining a lumen;
   a flange extending from the connector body between the proximal portion of the connector body and the distal portion of the connector body;
   a connecting device having an open configuration and a plurality of closed configurations, the connecting device comprising:
      first and second members pivotably attached together at one end by a hinge mechanism having one axis of rotation mounted to the flange, wherein the first and second members are configured to engage each other to secure the fluid conduit to the connector;
   wherein the plurality of closed configurations comprises a plurality of gaps between an inner surface of the first and second members and the outer surface of the proximal tubular body.

22. A kit for coupling tubular segments in a cardiovascular system, the kit comprising:

the connector of claim 6; and a tissue graft dilator configured to radially expand an end of the inflow component.

23. The kit of claim 22, further comprising a strain relief structure configured to couple with an end of the connector to form a slip fit with the inflow component for providing strain relief to the inflow component.

24. The kit of claim 23, further comprising a silicone sleeve disposed within the strain relief structure configured to be positioned about the inflow component.

25. The kit of claim 23, further comprising one or more inflow components and/or outflow components.

* * * * *